(12) United States Patent
     Wright

(10) Patent No.: US 10,368,873 B2
(45) Date of Patent: Aug. 6, 2019

(54) METHOD AND DEVICE FOR PRODUCING FOAM

(71) Applicant: PROVENSIS LIMITED, London (GB)

(72) Inventor: David Dakin Iorwerth Wright, London (GB)

(73) Assignee: Provensis Limited, London (GB)

( * ) Notice: Subject to any disclaimer, the term of this patent is extended or adjusted under 35 U.S.C. 154(b) by 117 days.

(21) Appl. No.: 15/641,585

(22) Filed: Jul. 5, 2017

(65) Prior Publication Data

US 2018/0008278 A1   Jan. 11, 2018

(30) Foreign Application Priority Data

Jul. 6, 2016 (GB) ..................................... 1611778

(51) Int. Cl.
     *B01F 5/10*    (2006.01)
     *B01F 3/04*    (2006.01)
     (Continued)

(52) U.S. Cl.
     CPC .. *A61B 17/12181* (2013.01); *A61B 17/00008* (2013.01); *A61B 17/12109* (2013.01); *A61K 9/122* (2013.01); *A61K 31/08* (2013.01); *A61M 37/00* (2013.01); *B01F 3/04* (2013.01); *B01F 3/04446* (2013.01); *B01F 5/0693* (2013.01); *B01F 5/0694* (2013.01); *B01F 5/10* (2013.01); *B01F 5/102* (2013.01); *B01F 15/0085* (2013.01); *B01F 15/0245* (2013.01); *B05B 7/0025* (2013.01); *A61B 2017/00526* (2013.01)

(58) Field of Classification Search
     CPC .............. B01F 5/10; B01F 3/04; A61M 37/00
     See application file for complete search history.

(56) References Cited

U.S. PATENT DOCUMENTS 5,676,962 A    10/1997  Cabrera Garrido et al.
8,235,935 B2 *  8/2012  Wright ................ B29C 44/3442
                                              261/29

FOREIGN PATENT DOCUMENTS

DE        3328530 A1 *  2/1985  ............. A62C 5/024
EP        0 656 203      6/1995
WO    WO 2008/075080    6/2008

OTHER PUBLICATIONS

L. Tessari; Nouvelle Technique d'Obtention de la Scléro-Mousse; *Phlebologie*, 2000, 53. No. 1.129.

* cited by examiner

*Primary Examiner* — Robert A Hopkins
(74) *Attorney, Agent, or Firm* — Finnegan, Henderson, Farabow, Garrett & Dunner, LLP

(57) ABSTRACT

The present invention relates to a device and method for making sclerosing foam, which is useful in the treatment of varicose veins and other venous conditions. The device comprises a continuous pathway that is at least partly formed of flexible or compressible material and that comprises a foam generating structure within the continuous pathway; the foam generating structure being formed of two or more elements, wherein each element defines at least one passageway of cross sectional area 1 µm2 to 10 mm2 and said two or more elements being arranged in series; a port which allows introduction of material into or extraction of material out of the continuous pathway; and a liquid pathway that is at least partly formed of flexible or compressible material and is arranged to deliver liquid into the foam generating structure between a first and second element of the foam generating structure.

13 Claims, 3 Drawing Sheets

Figure 1:
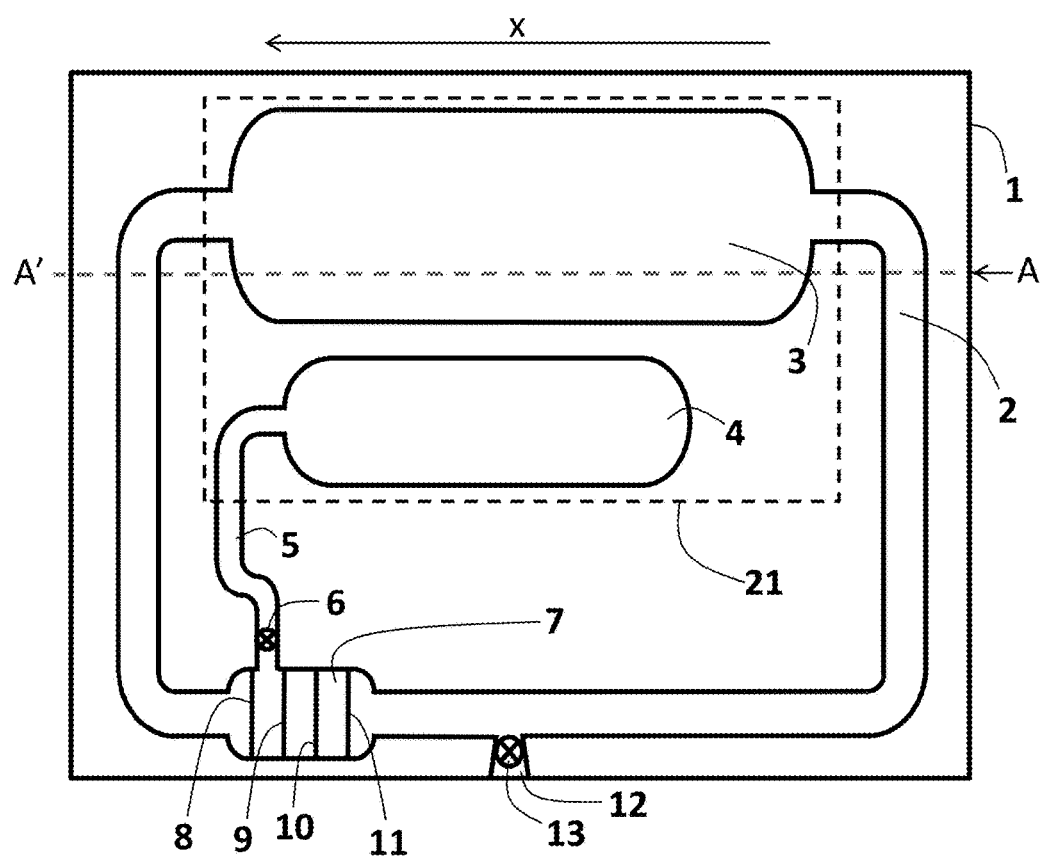

(51) Int. Cl.
*A61B 17/12* (2006.01)
*A61M 37/00* (2006.01)
*B01F 5/06* (2006.01)
*B01F 15/00* (2006.01)
*B01F 15/02* (2006.01)
*A61B 17/00* (2006.01)
*A61K 9/12* (2006.01)
*A61K 31/08* (2006.01)
*B05B 7/00* (2006.01)

METHOD AND DEVICE FOR PRODUCING FOAM

This application claims priority to GB Patent Application No. 1611778.0 filed 6 Jul. 2016, the entire content of which is hereby incorporated by reference.

The present invention relates to a device and method for mixing gas and liquid sclerosing agent to produce sclerosing foam which is suitable for intravenous administration to a patient. The invention is suitable, in particular, for producing sterile clinical grade sclerosing foam for use in the treatment of venous disorders e.g. varicose veins.

Intravenous administration of sclerosing foam is widely used in the treatment of varicose veins. Production of such foam requires mixing of sclerosant liquid, typically an aqueous solution of a sclerosing agent, with gas until foam is formed. It is often necessary to administer more than one dose of foam during a course of treatment and, since foams are dynamic systems, it is important that each dose of foam is of the same quality. It is also important that individual doses are prepared for administration without significant delay over the course of a treatment. The half-life of therapeutic foam is typically in the region of between 1 and 2.5 minutes, which is significantly shorter than the duration of most procedures, and therefore fresh doses of foam must be made as needed during each procedure. This introduces delays that reduce efficiency in patient treatment, and in some cases can result in administration of portions of foam having different properties in the course of a single treatment.

Traditional devices and methods for producing therapeutic foam facilitate mixing of gas and liquid to produce individual batches of foam. Such methods include the two syringe method described in Tessari (Tessari (2000). *Phlebologie* 53 (1); 129) and the rotating brush method described in Cabrera (EP-A-0656203 and U.S. Pat. No. 5,676,962), each of which produces foam of variable quality depending on the skills and experience of the user. Regardless of the consistency of foam quality produced using these methods, they are limited to the production of foam in individual batches, the volume of which is dictated by the size of the receptacle in which the foam is made.

WO2008/075080 describes a device in which gas and sclerosant liquid are circulated within a sealed chamber in the form of a closed loop comprising a foam generating structure, where they are mixed to form foam. The foam is then continuously circulated within the sealed chamber and through the foam generating structure to maintain its condition (i.e. the foam properties such as bubble size distribution, which directly affects foam half-life). This conditioning process is continued in order to ensure that foam remains properly mixed and to prevent the gas and liquid components from separating so that a ready supply of foam is available as needed during the course of a treatment. The properties of the foam (including density, half-life etc.) are controlled by pre-filling the chamber with known volumes and concentration of liquid and gas. Meeting the user's predefined properties requires that all liquid and gas in the sealed chamber is combined to form foam. However, in performing tests of a device made as described in WO2008/075080, the present inventor has found that liquid and/or gas may pool within the sealed chamber if they are not sufficiently mixed. In such cases a steady-state can be reached where at least a portion of the gas and liquid circulate separately in the chamber without effectively mixing. This can prevent formation of foam having the properties required and expected by the user.

Accordingly, there remains a need to provide a system in which rapid and complete mixing of liquid with gas is assured to produce therapeutic foam whose condition is maintained to allow withdrawal of individual doses as needed during the course of a treatment.

The present invention has improved foam generation over that described by WO2008/075080 (the contents of which are hereby incorporated by reference) by providing a continuous pathway in which liquid and gas first meet within a foam generating structure that ensures their immediate mixing, thereby preventing liquid or gas from pooling in the continuous pathway. This prevents a steady-state being reached where gas and liquid circulate separately in the chamber without effectively mixing to form foam. As a result, foam having desired properties is produced rapidly and efficiently, and the user can withdraw doses of foam with confidence that each dose of foam will have identical properties to the previously drawn dose. Furthermore, because the foam is continuously conditioned by passing through the foam generating device (i.e. after the initial mixing), the user can simply withdraw the desired volume of foam as needed such that delays during the course of a treatment are minimised.

Accordingly, in a first aspect the present invention provides a device for mixing gas and liquid to generate therapeutic foam as detailed in the claims below.

In use, gas is circulated within the continuous pathway, and liquid is introduced directly into the foam generating structure through the liquid pathway, a conduit for providing liquid into the foam generating structure, to promote immediate mixing of the liquid and gas to form foam. The user can then withdraw doses of foam as required through the access port in the continuous pathway.

The continuous pathway is a sealed hollow chamber defining an endless loop around which foam can circulate. Preferably the endless loop is generally circular or oval in shape. This is advantageous as it avoids geometries that might promote pooling of liquid, such as for example right angles or sharp corners, within the continuous pathway. The pathway has a predetermined maximum capacity and can accommodate predetermined volumes of gas and liquid that will be combined to produce foam. In other words the continuous pathway can expand and contract depending on the amount of gas and liquid added to it, however it cannot expand so much as to exceed the maximum capacity of the pathway. The pathway is formed of material that is impermeable to the gas being used to make the foam and also to the liquid being used to make the foam. Typically the pathway is formed of biocompatible plastic that is safe to use for preparation of pharmaceutical compositions to be administered to a patient. Suitable plastics comprise, for example, polypropylene, polyethylene, cyclopolyolefin, polycarbonate, polymethyl-methacrylate, polystyrene, polyvinyl chloride and acrylonitrile-butadiene-styrene copolymer (ABS). The pathway is at least partly formed of flexible or compressible material. This allows the volume of gas, liquid or foam within the pathway to be increased or decreased, within the predetermined maximum capacity of the pathway, without causing a pressure change within the pathway. Additionally, it permits deformation of at least a part of the continuous pathway to drive circulation of gas, liquid or foam within the pathway. Optionally, the pathway is at least partly formed of an elastic material. Suitable flexible or compressible materials include nylon, polyvinyl amide, polypropylene, polyethylene, polybutylene resin, thermoplastic elastomer and ethylene-vinyl acetate copolymer (EVA).

The continuous pathway may be formed by welding together two or more layers of gas-impermeable plastic, which encapsulate and retain the foam generating device and any required ports for introduction and extraction of materials. In this arrangement the device can be manufactured very simply, quickly and inexpensively. Welding of the plastic layers to form the continuous pathway can be achieved using any appropriate means, including for example heat or ultrasound. This allows for very simple engineering to be used to manufacture the device and to incorporate additional components within it as necessary. For example, welding together sheets of plastic over discrete, preformed components (foam generating device and valves/ports) would be easily achievable and inexpensive. Suitable gas-impermeable plastic materials include plastic laminates and metallised plastic laminates, for example aluminium plastic laminates. Laminates such as these are sufficiently gas impermeable, are readily weldable to form a continuous pathway, are sufficiently flexible to permit deformation in use and are sufficiently durable to endure typical manufacture and shipping processes.

The foam generating structure provides the means for mixing of gas and liquid by disrupting and/or restricting the flow of each within the continuous pathway. The foam generating structure is arranged within the continuous pathway such that substantially all of the contents of the pathway are forced through it as they are circulated within the pathway to prevent pooling of liquid and/or gas. The foam generating structure comprises more than one element, each element defining at least one passageway of cross sectional area 1 $\mu m^2$ to 10 $mm^2$, preferably 10 $\mu m^2$ to 5 $mm^2$, more preferably 50 $\mu m^2$ to 2 $mm^2$, through which gas and liquid pass when they are propelled through the pathway. The maximum dimension of the passage or passages is preferably between 0.1 $\mu m$ and 2 mm, more preferably between 1 $\mu m$ and 1 mm, more preferably between 2 $\mu m$ and 500 $\mu$, still more preferably between 3 $\mu m$ an 100 $\mu m$. The passage or passages is/are preferably provided by at least two elements comprising one or more meshes, screens or sinters. Preferably the said elements are spaced apart in the direction of flow by between 0.1 mm and 10 mm, preferably between 0.5 mm and 5 mm. The elements can be meshes, sinters or screens.

In a preferred embodiment, the foam generating structure is in the form of two or more, and ideally 3, 4, 5 or 6, such elements, arranged in series such that liquid is delivered directly into the foam generating structure at which point it mixes with gas, which is being driven through the foam generating structure and forms foam. In this embodiment, the foam generating structure is adapted to include a liquid pathway which provides sclerosing liquid directly into the foam generating structure between a first and second element to ensure the gas and liquid are mixed as they meet and pass through the second element. Further mixing and conditioning of the foam (i.e. filtering to create a desired bubble size distribution) occurs as the foam mixture passes through subsequent elements. This is advantageous as it ensures that the liquid is fed into a stream of gas to enable immediate mixing with gas and foam formation, thereby preventing unmixed liquid and gas from entering into the continuous pathway beyond the foam generating structure. In a preferred embodiment the liquid pathway is arranged in fluid communication with a foam generating structure in the form of four elements whereby liquid is delivered into the foam generating structure between the first and second element, as gas is passing through. This arrangement ensures immediate mixing and rapid foam formation within the foam generating element. In this embodiment the foam generating structure comprises four elements in the form of four Nylon 66 meshes held in high density polyethylene (HDPE) rings within an open-ended polypropylene casing. Such meshes typically have a diameter of 6 mm and have a 14% open area made up of 20 $\mu m$ pores, with the meshes spaced 3.5 mm apart. In alternative preferred embodiments, the same arrangement utilises meshes with smaller pore sizes, such as 5, 10 or 15 $\mu m$, as these smaller pore sizes have been shown to provide narrower bubble size distributions, which generally provides foam with longer half-lives.

The liquid pathway is a conduit for providing liquid directly into the foam generating structure. It is formed of material that is impermeable to the liquid being used to make the foam. Typically the pathway is formed of biocompatible plastic that is safe to use for preparation of pharmaceutical compositions to be administered to a patient. Suitable plastics comprise, for example, polypropylene, polyethylene, cyclopolyolefin, polycarbonate, polymethyl-methacrylate, polystyrene, polyvinyl chloride and acrylonitrile-butadiene-styrene copolymer (ABS). It is arranged such that liquid is delivered directly to the foam generating structure within the continuous pathway. Preferably it is arranged such that liquid is delivered into the foam generating structure such that it must pass through at least one element comprising one or more meshes, screens or sinters before leaving the foam generating structure. This ensures effective mixing with gas or foam so as to prevent unmixed liquid from pooling in the continuous pathway outside the foam generating structure. In particular embodiments it is arranged in fluid communication with the foam generating structure in the form of two or more, and ideally 3, 4, 5 or 6 elements such as meshes, sinters or screens, such that liquid is delivered from the liquid pathway between the first and second elements to ensure the gas and liquid are mixed by the second and subsequent elements to form foam. This is advantageous as it ensures that liquid is immediately mixed with gas on entering the foam generating structure, such that liquid is rapidly incorporated into foam and unmixed liquid cannot exit the foam generating structure. In a preferred embodiment the liquid pathway is in the form of tubing which extends from a reservoir of liquid and is arranged in fluid communication with the foam generating structure in the form of four elements (as described above) such that liquid can be delivered, under a driving force into the foam generating element between the first and the second element. This arrangement has been shown to provide immediate mixing and rapid foam formation within the foam generating structure. Ideally, the liquid pathway comprises a valve to ensure uni-directional flow of liquid and prevent back-flow of liquid or foam from the foam generating device into the liquid pathway.

The device may be provided with the continuous pathway empty or containing gas. Where the continuous pathway is empty, i.e. with no contents, the user can introduce whichever gas in whatever appropriate amount is required to produce foam with desired physical properties, e.g. density (approximated from the proportions of liquid and gas mixed at atmospheric pressure). This allows the user flexibility in using the device to generate foam with a desired gas composition and resulting foam density. The gas can be introduced into the pathway by any suitable means, but preferably it is introduced through the port which allows introduction of material into or extraction of material out of the continuous pathway, for example using a syringe. This simplifies the design and manufacture of the device by limiting the number of components to be incorporated into the device. Alternatively, the pathway is provided containing gas such that the user need only determine the volume of liquid that should be added to produce the desired foam. In certain embodiments the continuous pathway can be charged with a physiologically acceptable gas. This advantageously simplifies use of the device by removing the step of charging the pathway with gas, thereby reducing the risk of air contamination. A physiologically acceptable gas is a gas which may be substantially completely (i.e. more than 95%, preferably more than 99%) dissolved in or in other ways absorbed by the blood in a short period, i.e. less than 12 hours, preferably less than 1 hour. Examples of physiologically acceptable gases include oxygen, carbon dioxide, helium and mixtures thereof.

Optionally, the liquid pathway is at least partly formed of flexible or compressible material. This allows for introduction of liquid into the continuous pathway by mechanical deformation of a flexible or compressible part of the liquid pathway by a simple mechanical pump. For example, engagement of a flexible or compressible part of the liquid pathway by an inexpensive peristaltic pump can be used to deliver liquid into the gas forming structure of the device. Suitable flexible or compressible materials include nylon, polyvinyl amide, polypropylene, polyethylene, polybutylene resin, thermoplastic elastomer and ethylene-vinyl acetate copolymer (EVA).

The device may be provided with the liquid pathway empty or containing liquid. Where the liquid pathway is empty the user can introduce whichever liquid in whatever amount is required to produce foam with desired physical properties, e.g. density and concentration of sclerosing agent. This allows the user flexibility in using the device to prepare foams of sclerosing agent concentration which are suitable for the intended indication, e.g. high concentrations of sclerosing agent (e.g. 1-5% polidocanol) have been reported used in the treatment of large venous malformations whereas lower concentrations of sclerosing agents (e.g. 0.25-1% polidocanol) are typically used in the treatment of spider and reticular veins. The liquid can be introduced into the liquid pathway by any suitable means, for example it may be pumped from a source or reservoir or vial of sclerosant liquid, but preferably liquid is injected into the pathway, for example using a syringe. This simplifies the design and manufacture of the device by limiting the number of components to be incorporated into the liquid pathway. Alternatively, the liquid pathway can be charged with a particular volume and concentration of sclerosant liquid at the point of manufacture. This simplifies use of the device by removing the step of charging the liquid pathway with sclerosant liquid before preparing therapeutic foam for administration to a patient for sclerotherapy.

In certain embodiments the liquid pathway comprises a sealed container comprising sclerosant liquid, for example a single treatment vial. This simplifies use of the device by the treating physician. The sealed container can be opened manually by the user prior to using the device, or it can be opened on engagement with a pump or other external equipment that operates to force the liquid into the foam generating structure through the liquid pathway. This advantageously allows for simplified manufacture of the device because sclerosant liquid can be filled into sealed containers and sterilised separately before assembly of the liquid pathway within the device. Separate sterilisation in sealed containers also advantageously reduces the likelihood of oxidation reactions occurring during the sterilisation process that could impact sclerosant liquid composition. Additionally, provision of sclerosant liquid in preselected volumes and concentrations offers the user choice in achieving desired foam properties while avoiding the need to dilute sclerosant liquids at the point of use or the site of foam preparation.

A suitable sclerosant liquid is an aqueous solution of an irritant substance that causes a localised inflammatory reaction, favouring the elimination of abnormal veins in sclerotherapy. Sclerosant liquids include, e.g. a 1% aqueous solution of polidocanol, but other concentrations of polidocanol are possible, e.g. 0.25-5%, 0.25-1% or 1-5% and other suitable sclerosing agents include, e.g. sodium tetradecyl sulfate, ethanolamine oleate, sodium morrhuate, hypertonic glucosated or glucosaline solutions, glycerol, chromated glycerol or iodinated solutions.

Maintaining foam quality requires that all gas, liquid or foam remains in the continuous pathway and is circulated continuously within it until needed, and therefore it is important that foam does not flow back or reflux (i.e. reverse or retrograde flow) into the liquid pathway. This is typically achieved by the application of a continuous force to the liquid and continuous pathways, for example using a peristaltic pump, wherein the force applied to each pathway is the same. Additionally however, the device may further comprise a valve that prevents fluid flow into the liquid pathway from the foam generating structure and prevents reflux into the liquid pathway. Preferably, the valve is a one way valve that opens in response to increased pressure within the liquid pathway to allow liquid pass into the foam generating structure. The valve does not permit reverse flow or reflux of liquid, gas or foam in the direction away from the continuous pathway along the liquid pathway. This arrangement prevents reflux of liquid, gas or foam from the foam generating structure into the liquid pathway. Such reflux would be problematic as it could lead to sequestering of gas, liquid or foam in the liquid pathway, and this could impact foam properties, e.g. density, or it could reduce the volume of foam available for use in treating a patient. For the avoidance of doubt, reflux into the liquid pathway may be prevented by the application of a continuous force to the liquid pathway and by the inclusion of a valve within the liquid pathway.

The continuous pathway and the liquid pathway can be provided in separate housings or in a single common housing. Preferably, the continuous pathway and the liquid pathway are located in a common housing. This simplifies the device and its use. Additionally, this eases transportation and storage of the device by incorporating an additional covering (the housing) to protect device components during transport and storage. The common housing can form a disposable cassette or unit, or a consumable. Such a disposable cassette or unit, or consumable is advantageous because it allows for a single dose or single patient treatment to be provided in a single disposable unit.

The common housing, disposable or not, can comprise an aperture through which the continuous pathway may be engaged by a pump. This advantageously allows use of a rigid housing that eases handling of the device by users while allowing engagement of the device with an external pump to circulate foam within the continuous pathway. Additionally, in particular embodiments this provides for the use of a device which can be disposable together with a reusable pump to produce foam. Engagement with an external pump in this manner is desirable as it keeps the device costs low because internal pumping or circulating means are not required within the device. In preferred embodiments the aperture is aligned with a part of the liquid pathway that is formed of flexible or compressible material. This allows a simple pump, for example a peristaltic pump, to engage a mechanically deformable (flexible or compressible) part of the liquid pathway in order to deliver liquid to the foam generating structure. In such embodiments the same pump mechanism can simultaneously engage with mechanically deformable parts of the continuous pathway and the liquid pathway. This provides a simple mechanism for introduction of liquid into the foam generating structure to be timed so as to coincide with the arrival of gas being circulated in the continuous pathway. In particular embodiments the device additionally engages with an external means for limiting it to a single use. Advantageously, this prevents improper reuse of single use devices. External means for limiting to a single use include, for example, blades that rupture the continuous pathway on disengagement of the device from an external pump.

The device itself may comprise a pump adapted to circulate foam within the continuous pathway. Optionally, the pump is external to the continuous pathway and is adapted to engage with a part of the continuous pathway that is formed of flexible or compressible material in order to circulate the contents of the continuous pathway. This is advantageous because it reduces the cost of the device. A peristaltic pump is suitable for external engagement with the continuous pathway as described above. The inclusion of a peristaltic pump is particularly advantageous because it avoids direct contact between the pump and the foam produced in the device. In particular embodiments a peristaltic pump may externally engage the continuous pathway and the liquid pathway. This allows for simple, coordinated introduction of gas and liquid into the foam generating structure.

In a second aspect the present invention provides a method of generating therapeutic foam, the method comprising:

circulating gas within a continuous pathway that comprises a foam generating structure and introducing foamable liquid directly to the foam generating structure such that the gas and the liquid meet within the foam generating structure and mix to form foam.

In the method therapeutic foam is made in a closed system as described above.

As discussed above in connection with the first aspect of the invention, gas can be provided within a continuous pathway as manufactured and sold, or it may be introduced into a continuous pathway by the user. The foam can then be conditioned by continued circulation within the continuous pathway in order to ensure the foam is maintained in optimal condition so that the user can withdraw doses of foam from the continuous pathway as needed.

This method includes all of the advantages of the devices according to the first aspect of the invention as described in detail above. The method can be carried out using any device of the first aspect of the invention, and therefore the method can incorporate any of its features and offer all of its advantages as discussed above.

Further features and advantages of the invention will be apparent from the following description of specific embodiments, which is made with reference to the accompanying drawings.

FIG. 1 shows an embodiment in which laminate materials have been pressed and welded over a preformed foam generating device and valves to form the device of the invention.

Figure 2A:
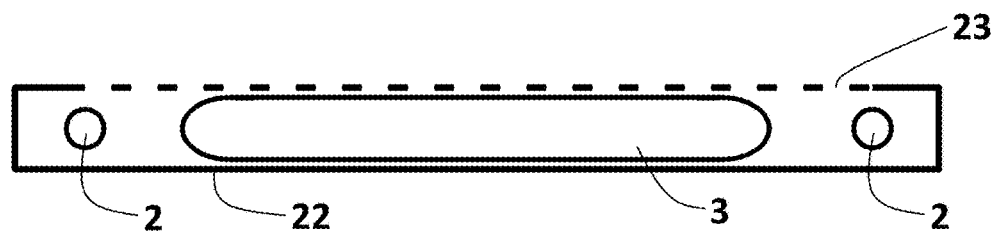
Figure 2B:
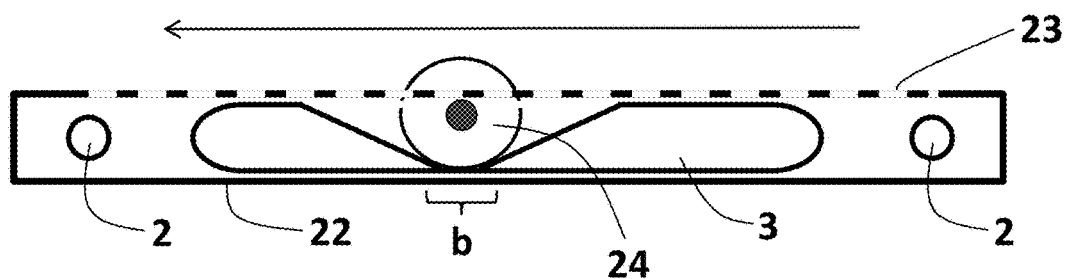

FIGS. 2A and 2B show a cross-sectional view along the plane identified by the dotted line A-A' shown in FIG. 1. FIG. 2A shows the cross-section view of the device charged with liquid and gas and ready for use. FIG. 2B shows a sectional view of the device in use and engaged by an external peristaltic pump.

A device of the invention is shown in FIG. 1 having a common housing (1), which is formed of laminate materials and which comprises all the components of the device. A continuous pathway (2) is created by pressing and welding of the laminate materials to define a pathway for the circulation of foam and foam constituents within the device. The continuous pathway (2) is formed of compressible material but need only includes an expanded volume portion (3) formed of compressible material within the pump contact patch (21) such that movement of a pump roller (see FIG. 2B) across the pump contact patch (21) deforms the portion (3) to force foam or foam constituents around the continuous pathway (2). The continuous pathway (2) is formed by pressing of the laminate materials around a foam generating structure (7) to ensure that sealed, fluid communication is achieved between the continuous pathway to ensure that contents are delivered into the foam generating structure without leaking. The foam generating structure (7) comprises a series of four filter meshes (8), (9), (10) and (11), each having an average cross section area of between 3 and 80 mm$^2$ arranged at a right angle (90°) to the direction of flow of foam within the structure (7).

Sclerosant liquid is provided in liquid chamber (4), which is also formed of compressible material and is situated within the pump contact patch (21) so that, on initial contact, a single peristaltic pump can be utilised to drive liquid out of the liquid chamber at the same time as driving gas from the expanded volume portion (4) (which acts as a gas reservoir before use). Physiological gas is already present (filled at the point of manufacture) or is introduced into the continuous pathway (2) through the access port (12). Under normal atmospheric pressure the one way valve (6) prevents ingress of gas into the liquid chamber (4) through the liquid pathway (5), and valve (13) effectively isolates the continuous pathway (2) from the external environment to prevent leakage of gas or foam. In use, one way valve (6) opens under pressure to allow liquid pass along the liquid pathway (5) into the foam generating structure (7).

In use, the device engages a peristaltic pump (not shown). A peristaltic pump roller (24) (see FIG. 2B) contacts the device and applies a continuous force to the continuous pathway (2) and to the liquid chamber (4) and pathway (5) as it moves in the direction of arrow "x" across the pump contact patch (21). This provides sufficient pressure to prevent reflux (i.e. reverse or retrograde flow) into the liquid pathway. On initiating use, the roller (24) contacts the continuous pathway (2) that contains physiological gas, and as it moves across the portion (3) it initiates circulation of gas within the continuous pathway (2).

As the roller (24) continues to move it engages the liquid chamber (4) and forces sclerosant liquid along the liquid pathway (5) and through one way valve (6) into the foam generating structure (7). The sclerosant liquid is introduced into the foam generating structure (7) between the first filter mesh (8) and second filter mesh (9) where it meets the gas circulating in the continuous pathway (2). Passage of gas and liquid together through the second filter mesh (9), third filter mesh (10) and fourth filter mesh (11) allows efficient mixing of gas and liquid to form foam before any liquid leaves the foam generating structure (7). This prevents liquid from pooling within the continuous loop (2).

On completing its track along the length of the contact patch, the roller (24) is raised and loses contact with the device as it returns along a determined track to reinitiate contact with the device and propel foam through the continuous pathway (2). Importantly, the contact patch is defined so that the roller applies pressure along the entirety of the expanded volume portion (3) and ensures that it is emptied by each pass of the roller. A peristaltic pump typically has at least two rollers that follow each other at set intervals such that one roller is in contact with the device at all times while the device is in use. This arrangement ensures that there is constant contact between the pump and the device in order to maintain unidirectional flow and to prevent reflux of gas or foam within the continuous pathway.

The peristaltic pump continually circulates the foam within the continuous pathway (2) to condition and maintain it within the desired specification of the user. When the user is ready to administer foam to a patient a suitable dose of foam is withdrawn from the continuous pathway (2) through the access port (12). The one way valve (6) prevents reflux of foam and foam constituents into the liquid pathway (5) from the continuous pathway (2) while the pump is inactive. Optionally, the pump may be stopped while the required dose of foam is withdrawn, but this is not essential. Once foam withdrawal is complete the user restarts the pump, and the remaining foam continues to circulate within the continuous pathway (2). In this way the foam is kept in optimal condition and remains ready for withdrawal of further doses and administration to patients as required.

A cross section along the plane provided by the line A-A' shown in FIG. 1 is provided in FIG. 2A. In this embodiment the common housing (22) is provided in the form of a hard plastics cassette which contains the components of the device as shown in FIG. 1, including the continuous pathway (2) and the portion formed of compressible material (3). The housing (22) is provided with an aperture (23) that is arranged so as to permit contact between an external pump (not shown) and the expanded volume portion (3). A cross section of the same device is shown in engagement with an external pump in FIG. 2B. A peristaltic pump roller (24) is shown in contact with the device and applying a continuous force at point "b" across the propulsion chamber (3). As the roller (24) moves in the direction of the arrow so too does the point "b", and this effectively pushes the contents of the propulsion chamber (3) through the continuous pathway (2) such that they eventually return to the chamber (3).

The invention claimed is:

1. A device for mixing gas and liquid to generate therapeutic foam, comprising:
    a continuous pathway that is at least partly formed of flexible or compressible material and that comprises a foam generating structure within the continuous pathway; the foam generating structure being formed of two or more elements wherein each element defines at least one passageway of cross sectional area 1 $\mu m^2$ to 10 $mm^2$ and said two or more elements being arranged in series;
    a port which allows introduction of material into or extraction of material out of the continuous pathway; and
    a liquid pathway that is at least partly formed of flexible or compressible material and is arranged to deliver liquid into the foam generating structure between a first element and second element of the foam generating structure.

2. A device according to claim 1 wherein the continuous pathway and the liquid pathway are formed by welding together of two or more layers of gas-impermeable plastic.

3. A device according to claim 1 wherein the continuous pathway is charged with physiologically acceptable gas.

4. A device according to claim 1 wherein the liquid pathway is charged with sclerosant liquid prior to use.

5. A device according to claim 4 wherein the liquid pathway comprises a sealed container.

6. A device according to claim 1 further comprising a valve that regulates fluid communication between the liquid pathway and the foam generating structure.

7. A device according to claim 1 wherein the continuous pathway and the liquid pathway are located in a common housing.

8. A device according to claim 7 wherein the housing is in the form of a disposable cassette, unit or consumable.

9. A device according to claim 7 wherein the housing comprises an aperture through which the continuous pathway may be engaged by a pump.

10. A device according to claim 1 further comprising a pump adapted to circulate foam within the continuous pathway.

11. A device according to claim 10 wherein the pump is adapted to engage with a part of the continuous pathway and the liquid pathway that are formed of flexible or compressible material.

12. A method of generating therapeutic foam using a device according to claim 1.

13. A method of generating therapeutic foam, the method comprising circulating gas within a continuous pathway that comprises a foam generating structure and introducing foamable liquid directly to the foam generating structure such that the gas and the liquid meet within the foam generating structure and mix to form foam.

* * * * *